United States Patent [19]
Wilkinson

[11] Patent Number: 5,484,366
[45] Date of Patent: Jan. 16, 1996

[54] AEROBIC/CROSS TRAINING EXERCISE BELT

[76] Inventor: William T. Wilkinson, P.O. Box 572, Crownsville, Md. 21032-0572

[21] Appl. No.: 312,691

[22] Filed: Sep. 27, 1994

Related U.S. Application Data

[63] Continuation of Ser. No. 35,636, Mar. 23, 1993, abandoned, which is a continuation-in-part of Ser. No. 972,251, Nov. 5, 1992, abandoned.

[51] Int. Cl.$^6$ ............................................. A63B 21/065
[52] U.S. Cl. ...................... 482/105; 482/124; 607/114; 607/108
[58] Field of Search .................. 2/64; 482/124, 482/126, 105, 121, 106; 607/106–108, 109–114

[56] References Cited

U.S. PATENT DOCUMENTS

| | | | |
|---|---|---|---|
| 866,495 | 9/1907 | Marks | 482/124 |
| 1,618,273 | 2/1927 | Davidson . | |
| 2,298,361 | 10/1942 | Freund | 607/108 |
| 2,678,447 | 5/1954 | Bracken . | |
| 4,591,150 | 5/1986 | Mosher et al. | 482/125 |
| 4,813,080 | 3/1989 | Toso . | |
| 4,955,608 | 9/1990 | Dougherty et al. | 482/124 |
| 4,993,409 | 2/1991 | Grim . | |
| 5,002,270 | 3/1991 | Shine | 482/105 |
| 5,007,412 | 4/1991 | Dewall . | |
| 5,062,414 | 11/1991 | Grim . | |
| 5,062,642 | 11/1991 | Berry et al. | 482/124 |
| 5,067,484 | 11/1991 | Hiemstra-Paez | 482/105 |
| 5,072,455 | 12/1991 | St. Ours . | |
| 5,105,806 | 4/1992 | Woodhouse et al. . | |
| 5,203,754 | 4/1993 | Maclean | 482/124 |
| 5,207,635 | 5/1993 | Ricards et al. | 482/124 |
| 5,308,779 | 8/1993 | Barry et al. . | |

FOREIGN PATENT DOCUMENTS

| | | | |
|---|---|---|---|
| 4002071 | 6/1984 | WIPO | 607/108 |

OTHER PUBLICATIONS

Heathcore by Omnipak by Dr. Kirt Josefek, Cambridge, Mass. 02139 (no priority date).

Primary Examiner—Richard J. Apley
Assistant Examiner—Jerome Donnelly
Attorney, Agent, or Firm—Connolly & Hutz

[57] ABSTRACT

A belt comprising a straight piece of material having a faster on each end whereby the ends can be fastened together to form a closed belt. A back lumbar support is connected to the rear body of the belt. The back lumbar support has at least one pocket to mount chemical gel-packs whereby the user would have a thermal application to the lumbar area while wear wearing the belt. A body garment that contains permanent or detachable gel pack containers. The gel packs may be heated or cooled to the desired temperature. The body garment may contain permanent and detachable sleeves.

18 Claims, 2 Drawing Sheets

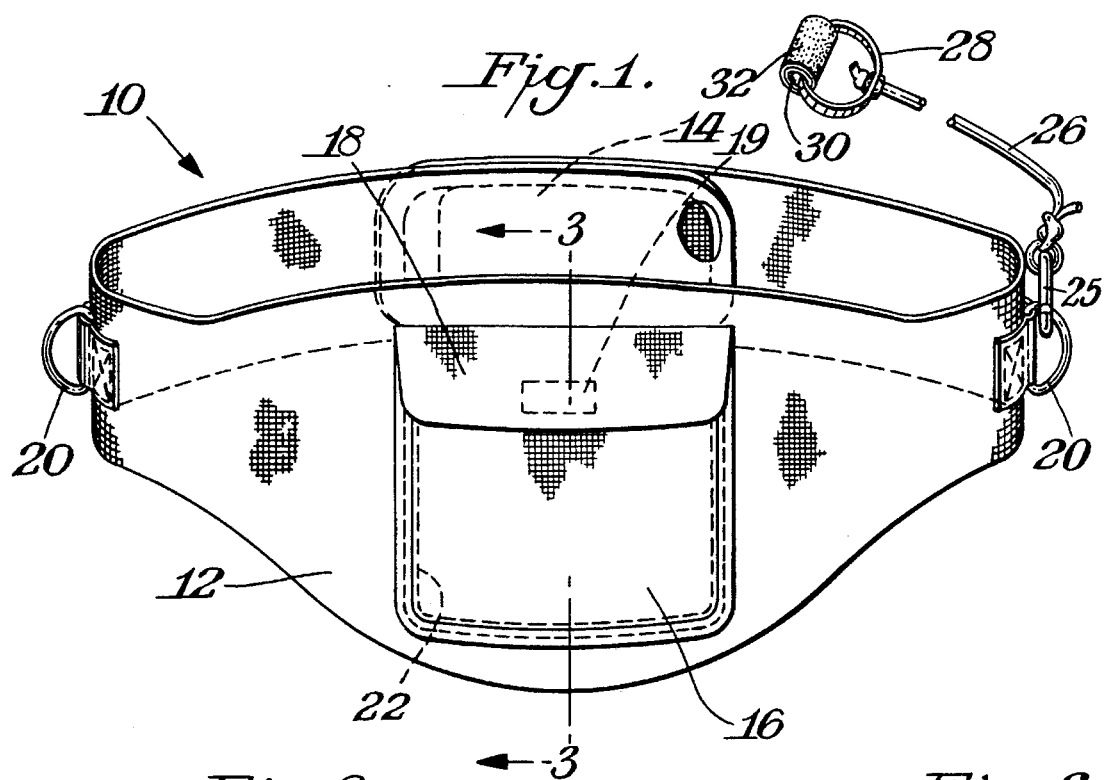
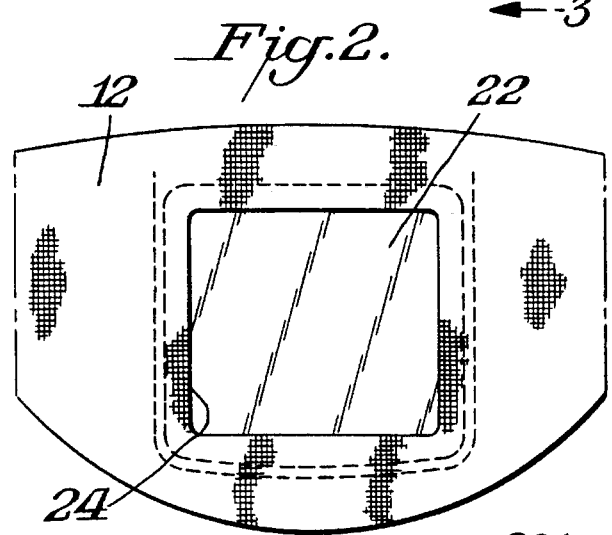
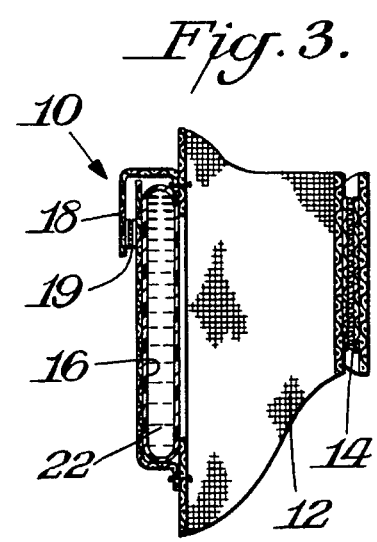
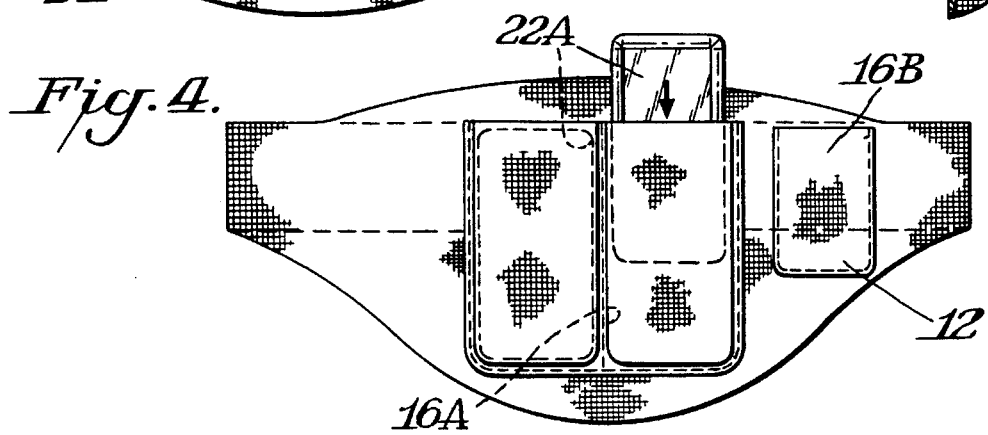

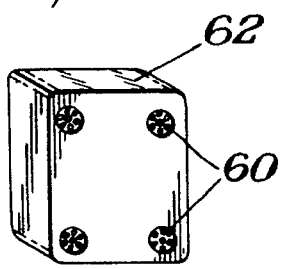
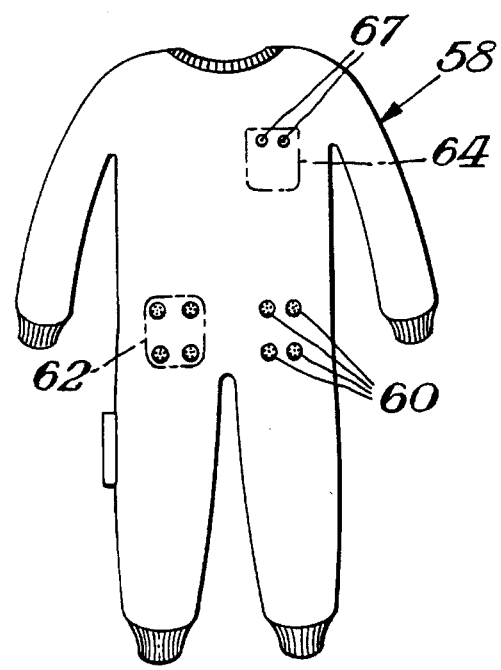
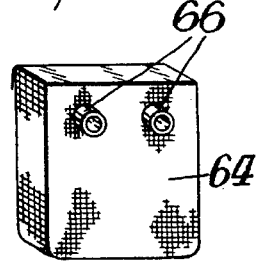
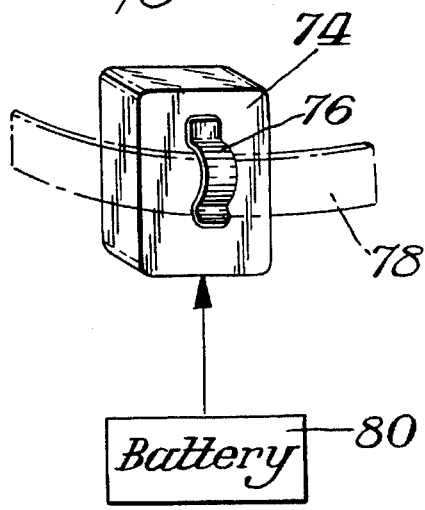
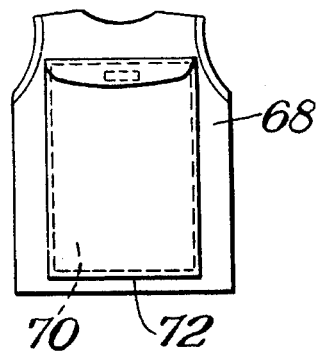

AEROBIC/CROSS TRAINING EXERCISE BELT

CROSS-REFERENCE TO RELATED APPLICATION

This application is a continuation of application Ser. No. 08/035,636 filed on Mar. 23, 1993, now abandoned, which is a continuation-in-part of Ser. No. 07/972,251, which was filed Nov. 5, 1992 entitled Aerobic/Cross Training Exercise Vest, now abandoned.

BACKGROUND OF THE INVENTION

Many people today have back problems. Work belts providing back support have become a very integral part of today's society. These belts provide support for the back and enable people to move with comfort. These belts are now being required to be worn by many employers of hardware stores and automotive shops in order to eliminate employees receiving serious back problems. These belts are often worn by people sitting at spectator events when they have to sit for a long, extended period of time. However, there is a problem with these belts in that these belts do not provide heat or cold temperatures.

U.S. Pat. No. 5,072,455 issued to St. Ours describes a belt having on at least one surface having one or more pockets to receive replaceable packets of refreezable material. The gel is refreezable only. In addition, this belt does not supply a lumbar support. The belt is used to reduce the body temperature in a hot environment.

U.S. Pat. No. 4,993,409 issued to Grim describes a back support of elastic material which carries a gel pad and an air bladder. The gel pad may be used for heating or cooling. The air bladder must be present.

It would be desirable if such devices could also provide a back support while doing the exercise program or daily activities such as walking, sitting etc. Additionally, it would be desirable if such device could conveniently function to hold personal objects of the user.

SUMMARY OF THE INVENTION

An object of this invention is to provide an aerobic exercise belt which satisfies the above needs.

A further object of this invention is to provide a belt which particularly provides a lumbar support and offers the feature of having inserting either hot or cold gel packs into the back of the belt in order to supply warmth or chill to the users lower back. The belt may, in addition, have pockets for storage of portable radios, cassette players, compact disc players, etc. and rings for storing exercise cables, keys, tools, lights, etc.

A further object of this invention is to provide a body garment which provides lumbar back support and offers features of inserting either hot or cold gel packs into the back of the body garment. The body garment may additionally have pockets for storage of portable radios, cassette players, compact disc players etc., and rings for storing exercise cables, keys, tools, lights, etc.

BRIEF DESCRIPTION OF THE DRAWINGS

FIG. 1 is a front elevation view of a belt in accordance with this invention.

FIG. 2 is an inside elevation view of a lower back support showing the opening to the gel-pack compartment.

FIG. 3 is a cross-sectional view taken along line 3—3 of FIG. 1.

FIG. 4 is a back elevational view of another lumbar back support showing two gel-pack compartments.

FIG. 5 is a rear elevational view of a full-body garment illustrating various types of gel pack attachments.

FIG. 6 is a rear perspective view of gel packs having a tape fastener system (e.g., a hook and loop type fastener of the type available under the tradename VELCRO® pads for attachment of full body garment as shown in FIG. 5.

FIG. 7 is a rear perspective view of gel packs in attachable pockets that snap onto the garment shown in FIG. 5.

FIG. 8 is a rear elevational view of vest showing a large gel pack in a large attachment pack.

FIG. 9 is a rear perspective view of a gel pack attached to a belt by a belt clip.

DETAILED DESCRIPTION OF THE DRAWINGS

FIG. 1 depicts a belt 10 in the front view in accordance with this invention. The belt 10 is made of a one-piece material 12 that could be breathable such as an air-permeable mesh-type fabric. The belt 10 could also have a detachable, washable inside liner (not shown). The front of the belt 10 is completely open. The belt 10 is closed by a fastening means 14. The fastening means 14 could be but is not limited to VELCRO®, as depicted in FIG. 1 or snaps, zippers, belt buckles, etc. The belt 10 is held snugly to the exerciser by the use of the fastening means 14. The belt 10 could be at least 4 inches wide and preferably between about 7 to about 12 inches wide and could wrap around the user's midsection. The belt 10, in addition could have a series of one and preferably a plurality of back pockets 16 fastened to the back of the belt. The back pockets 16 can be detachably fastened to the belt by VELCRO®, or permanently sewn on or any other conventional fastening means. Also fastened to the belt 10 could be a series of loops 20. The pockets 16 could be used for storing the gel-pack 22. Each pocket would have a flap 18 that would have a fastening means 19 such as VELCRO® as depicted in FIG. 1 or snaps, straps, etc. The belt advantageously would be capable of being used with bands, storing keys, tools, lights, etc. fastened to the ring 20. Exercise cords 26 can be permanently or detachably attached to said ring 20. A fastener 25 would connect to the ring 20. The fastener 25 could be any conventional fastener, such as a clip. The fastener 25 could have a hole at one end. The hole could be larger in diameter than the elastic cord 26. The elastic cord 26 would fit inside the hole of the fastener 25. The fastener 25 would thereby connect the elastic cord 26 to the ring 20. The elastic cord 26 would fit inside the hole of the fastener 25 or be connected to the fastener 25 through the hole. The elastic cord 26 would be connected to a handle 28. The handle 28 could be made of any suitable material such as, but not limited to plastic, fabric, rubber, cloth, or any other suitable material. Attached to the handle 28 could also be a grip 30 made of any suitable material such as, but not limited to a cylindrical shape piece of polyvinyl chloride (PVC). The grip 30 could be covered with padding 32. The padding 32 could be made of any suitable material such as, but not limited to foam, rubber or cloth. The exercise cords could also be the ones from U.S. Pat. No. 5,141,223, issued Aug. 25, 1992 to Stephen I. Block which is incorporated by reference.

FIG. 2 shows an inside elevation of the lumbar back support having an opening 24 to the gel-pack compartment. The opening to the gel-pack compartment would allow the gel pack to fit next to and contact the user's back. The gel-pack would be made of a chemical material such as commercially available heat packs or ice packs. These packs would be placed in the pocket 16 in the back of the belt. The gel-pack 22 could either be made of a refreezable material or be capable of heating when used.

FIG. 3 is a cross-sectional view taken along the 3—3 line of FIG. 1. FIG. 3 shows the belt fastening means 14, the belt 12, the pocket 16 and the pocket fastening means 18.

FIG. 4 illustrates a back elevation of another lumbar support showing two gel-pack compartments. The gel-packs 24 can be inserted into the back of the compartments 16A. In addition, there can be a series of compartments having at least one to what ever maximum number will fit in the back. The chemical gel-packs slide in the back into the pouches. There could also be a pocket 16B that can be used to store radios, cassette payers, compact disc players, wallets, keys, etc. The pocket can be placed anywhere on the belt. The pocket 16B would preferably be mounted to the rear of the belt as shown in FIG. 4.

FIG. 5 shows a rear elevational view of a full body garment 58. The body garment 58 has a series of fastening means 60 attached to various locations of the body garment 58. The fastening means 60 can be any known fastening means such as hook and loop fasteners marketed as VEL-CRO® pads as shown in FIGS. 5 and 6 or snaps 66 as shown in FIG. 7. The body garment 58 can come in various sizes to fit the user. The body garment 58 can be made of various types of materials. The material can be breathable nylon or can be similar to a sauna suit, etc. The body garment 58 can be a modified version of the embodiments described in U.S. Pat. No. 5,176,600 or the embodiments described in Ser. No. 788,365 filed Nov. 6, 1991 which are incorporated herein by reference.

In the preferred practice of the invention, a one or two piece garment is made of a suitable elastic, stretchable, resilient material, such as Lycra® which may be in the form of a complete body suit or a shirt or pants type garment. It would also be possible to have reinforced elastic areas with panels joining the sleeves or arms to the torso and joining the legs to each other. Webs or panels would be shaped and located in accordance with the characteristic exercise motion which is intended to provide the desired resistance to the normal back and forth motion of the arms and legs during the main aerobic exercise program, such as walking, step climbing, jogging, running, or other forms of exercise, including swimming, cycling, yoga, dancing, ice or roller skating, aerobic warm-ups, etc. The panels or webs can have an suitable means of attachments, including zippers, snaps, hooks/loops so that the webs are detachable on one or more sides thereby permitting the user to engage the resistance when it is desired to supplement the main exercise program with more aerobic exercise. Additionally, the user may thereby adjust the level of aerobic exercise by the selective engagement of one or more panels. Alternatively, the user may completely disengage the webs or panels so that there is no supplement to the main exercise program.

The garment may also be provided with pockets so that weights could be added to further vary the load/resistance on the user. By adding such weights and resistance the user can thereby develop a progressive aerobic exercise program and the garment is thus adapted to all strength, age and sex individuals. Further, the combination of adjustable resistance and weights allows the user to tune the exercise load to the correct feel or comfort and control the amount of exercise achieved in a given period of time.

FIG. 5 additionally shows the gel packs placed inside a gel pack container 62. The gel pack container 62 can be attached around the lower back, upper back, lower legs (not shown), etc. The gel pack container 62 or the gel packs could be attached to the garment 58 by any known fastening means 60 such as but not limited to snaps or VELCRO®.

Additionally, there can be one or more permanent or detachable pockets 64 attached to the garment 58. The detachable pocket could be attached by any fastening means 67 such as but not limited to VELCRO® or snaps (as shown in FIG. 5). The pocket 64 can be used to store items such as radios, cassette players, compact disc players, wallets, keys etc. In addition, the garment could also have rings fastened to the front or back of the garment. The rings could be used for storing exercise cables/cords, keys, tools, lights, exercise/walking poles, etc.

FIG. 6 shows a gel pack placed inside a gel pack container 62 having a series of fastening means 60 such as VELCRO® pads. In FIG. 6, the fastening means 60 are placed in at least one location in the gel pack container. The fastening means 60 could be placed in equal positions in all four corners. However, they can also be placed in the center of the gel pack and having one big fastener or there could be just two fasteners.

FIG. 7 illustrates the detachable pocket 64 which could hold the gel packs having a snap attachment 66. The detachable pocket 64 would have a fastening means on the back of the pocket. The fastening means 66 could be but is not limited to VELCRO®, snaps as depicted in FIG. 7. The fastening means 66 could include the snap attachment. The snap attachment would snap into the suit thereby making these detachable pocket gel packs.

FIG. 8 is a rear elevational view, of a vest 68 having a large gel pack 70 and a large attached pocket 72. The vest 68 could be made of a single piece of material. The vest 68 would preferably open and close in the front. The rear of the vest could have a large pocket 72 which can be permanent or removable. The large pocket 72 can cover most of the surface are of the back. The gel pack 70 would fit inside the large pocket 72.

FIG. 9 is a rear perspective view of a gel pack attachment 74 to a belt 78 by a belt clip 76. In addition, a battery 80 and simple circuitry may be installed into the gel pack attachment thereby heating and keeping the gel pack at a constant heated temperature. In this embodiment, the user could use a series of gel pack attachments attached to the belt, thereby providing heat or cold to the lower back of the body. The batteries would enable the gel pack to stay hotter longer. To heat the gel packs, the user can put the gel packs in the microwave and heat them to the desired temperature and then insert them into the gel pack compartment.

This invention may be practiced in a varied number of different ways as mentioned above. The gel packs may be permanently fixed to the body garment, belt or vest or the gel packs may be detachable. Storage pockets and tings/loops may be attached to the body garments, belts or vests. The gel packs may be heated (such as in a microwave) or cooled such as in a freezer.

What I claim:

1. An aerobic/cross training belt comprising:

a belt having a first end and a second end configured to encircle a user's waist, said belt having a first means for fastening on said first end and a complementary fastening means on said second end and being configured to engage said first means whereby the ends can be fastened together to form a closed loop belt, a lumbar support positioned between said ends of said belt at a rear body of said belt so as to support the lumbar of a user when the ends of said belt are positioned on a forward facing frontal area of a user, said lumbar support including at least one pocket means containing at least on thermal gel-pack, at least one attachment means attached to said belt between the lumbar support and an end of the belt, at least one elongated resilient member having ends, a first end of said resilient member being fastened to said attachment means and a second end of said resilient member being connected to a means configured to be engaged by a user, whereby a user may perform an exercise by pulling on said means for engaging while simultaneously receiving support and thermal therapeutic treatment at a lumbar region of the user.

2. The belt as claimed in claim 1, wherein said thermal gel-pack is a heat pack.

3. The belt as claimed in claim 1, wherein said thermal gel-pack is a chemical pack that is an icepack.

4. The belt as claimed in claim 1, wherein there are at least two pockets which can contain the gel-packs.

5. The belt as claimed in claim 1, wherein said attachment means is a ring.

6. The belt as claimed in claim 5, wherein said elongated resilient member having ends is detachably attached from said ring.

7. The belt as claimed in claim 5, wherein said elongated resilient member is permanently attached to said ring.

8. The belt as claimed in claim 1, wherein part of the pocket and belt have a hole whereby the thermal gel-pack slides into the pocket and the thermal gel-pack contacts the body of the user, through the hole.

9. The belt as claimed in claim 1, wherein said belt is made of a one-piece material that is breathable.

10. The belt as claimed in claim 9, wherein said breathable material is an air-permeable, mesh-type fabric.

11. The belt as claimed in claim 1, further comprising a detachable, washable inside liner.

12. The belt as claimed in claim 1, wherein said fastening means is by a hook and loop type fastener.

13. The belt as claimed in claim 5, wherein said fastening means is a hook and loop-type fastener and said belt further comprises a detachable, washable inside liner.

14. The belt as claimed in claim 1, wherein one end of said elongated resilient members is fastened to a ring on said belt and the other end of the elongated resilient member is attached to a handle.

15. The belt as claimed in claim 14, wherein said handle has a padded grip.

16. The belt as claimed in claim 15, wherein said padded grip is foam.

17. The belt as claimed in claim 1, wherein said attachment means is two rings connected to said belt wherein each ring contains one elongated resilient member.

18. The belt as claimed in claim 13, wherein said attachment means is two rings connected to said belt wherein each ring contains one elongated resilient member.

* * * * *